United States Patent
Andrews

(10) Patent No.: US 10,551,362 B2
(45) Date of Patent: Feb. 4, 2020

(54) METHOD FOR EXTENDING THE DYNAMIC RANGE OF ABSORBANCE DETECTORS

(71) Applicant: Waters Technologies Corporation, Milford, MA (US)

(72) Inventor: Richard W. Andrews, Rehoboth, MA (US)

(73) Assignee: Waters Technologies Corporation, Milford, MA (US)

( * ) Notice: Subject to any disclaimer, the term of this patent is extended or adjusted under 35 U.S.C. 154(b) by 787 days.

(21) Appl. No.: 14/779,274

(22) PCT Filed: Mar. 19, 2014

(86) PCT No.: PCT/US2014/031186
§ 371 (c)(1),
(2) Date: Sep. 22, 2015

(87) PCT Pub. No.: WO2014/160568
PCT Pub. Date: Oct. 2, 2014

(65) Prior Publication Data
US 2016/0054275 A1    Feb. 25, 2016

Related U.S. Application Data

(60) Provisional application No. 61/805,210, filed on Mar. 26, 2013.

(51) Int. Cl.
| | | |
|---|---|---|
| *G01N 30/62* | (2006.01) | |
| *G01N 30/74* | (2006.01) | |
| *G01N 30/86* | (2006.01) | |
| *G01N 21/27* | (2006.01) | |
| *G01N 21/31* | (2006.01) | |
| *G01N 21/59* | (2006.01) | |

(52) U.S. Cl.
CPC .......... *G01N 30/74* (2013.01); *G01N 21/274* (2013.01); *G01N 21/3103* (2013.01); *G01N 21/59* (2013.01); *G01N 30/8665* (2013.01); *G01N 30/8631* (2013.01); *G01N 2030/862* (2013.01); *G01N 2201/127* (2013.01)

(58) Field of Classification Search
CPC ................. G01N 30/74; G01N 21/274; G01N 2030/623; G01N 30/62; G01N 30/86; G01N 2030/862; G01N 30/8696; G01N 21/3103; G01N 21/59
USPC ........................................................ 356/440
See application file for complete search history.

(56) References Cited

U.S. PATENT DOCUMENTS

| | | | |
|---|---|---|---|
| 5,315,528 A | 5/1994 | L'vov | |
| 6,122,052 A * | 9/2000 | Barnes | G01J 3/28 |
| | | | 356/328 |

(Continued)

OTHER PUBLICATIONS

International Search Report, PCT/US2014/031186 dated Nov. 5, 2014.

*Primary Examiner* — Rebecca C Bryant

(57) ABSTRACT

The invention generally provides methods for improving the dynamic range of an absorbance detector and absorbance detectors having improved dynamic range. In an exemplary embodiment, the method includes receiving calibration data for a plurality of samples, the calibration data comprising an absorbance for a concentration of each of the samples, calculating a contribution of stray light to the calibration data, and correcting subsequent data by removing the contribution of stray light.

13 Claims, 5 Drawing Sheets

(56) References Cited

U.S. PATENT DOCUMENTS

2002/0001851 A1    1/2002   Degrandpre
2005/0279924 A1   12/2005   Ridder
2013/0071869 A1    3/2013   Wu

* cited by examiner

METHOD FOR EXTENDING THE DYNAMIC RANGE OF ABSORBANCE DETECTORS

RELATED APPLICATION

This application is the National Stage of International Application No. PCT/US14/031186, filed Mar. 19, 2014, which claims the benefit of U.S. Provisional Application No. 61/805,210, filed Mar. 26, 2013. The foregoing applications are incorporated herein by reference.

FIELD OF THE INVENTION

The present invention generally relates to absorbance detection in chromatography, and in particular, to extending the linear dynamic range of absorbance detectors for use in liquid chromatography.

BACKGROUND

Liquid chromatography systems are used to carry out chemical separations. A typical liquid chromatography system consists of the following major components: a pump, an injector, a column, and a detector. The pump compels a mobile phase, for example, a solution, through a fluid path comprising an injector, column and a detector. The injector permits the introduction of samples into the fluid stream above the column. The column contains a packed bed of media. The media is normally porous and relatively inert. Compounds in the sample will exhibit a characteristic affinity to the media. That is, some compounds exhibit high affinity and some compounds exhibit low affinity. As a result, as the compounds are carried through the media, the compounds separate into bands which elute or come off the column at different times. These bands are detected by the detector.

Absorbance detectors are one exemplary type of detector that can be used to detect the bands eluting from the column. Broad spectrum or bandwidth limited light is directed through a sample, and then measured at the chosen analytical wavelengths by a detector, such as a photodetector. In these instruments, light traverses a fixed distance (a path length) through the sample. The instrument's photodetector signal is measured when the analyte sample concentration is zero ($I_0$) and when the analyte is present (I). Absorbance (A), a dimensionless number commonly expressed in absorbance units (AU) for convenience, is calculated from $\log(I_0/I)$ and displayed as the instrument output. Absorbance is proportional to the product of path length (b) and concentration (c). This relationship between absorbance, path length, and concentration is known as Beer's Law. A constant of proportionality can be found from a calibration experiment using known analyte concentrations, thus enabling unknown concentrations to be measured. If path length is expressed in centimeters (cm) and concentration in moles per liter (moles/L), then the proportionality constant is called the molar absorbtivity ($\varepsilon$) with units $cm^{-1}$ $(moles/L)^{-1}$.

Since the molar absorbtivity, $\varepsilon$, varies with wavelength for any analyte, the instrument can include a monochromator, filters, a diode array spectrograph or, in the case of the infrared, a Fourier transform interferometer, to measure absorbance at specific wavelengths.

The range of analyte concentrations that can be measured by an absorbance detector is limited. At the low end, the minimum detectable change in absorbance is set by the baseline noise on the absorbance output, a value which varies from wavelength to wavelength and from instrument to instrument. For example, a well-designed UV absorbance detector for HPLC can detect an absorbance change in the range of about 10µ AU to about 20µ AU. An upper limit of concentration measurement is reached when the relationship between absorbance and concentration becomes significantly nonlinear. This typically occurs when absorbance exceeds about 1 to about 2 AU. The upper absorbance limit is usually the result of stray light or inadequate spectral resolution. The upper absorbance limit varies with wavelength and from instrument to instrument, and is reduced if the solvent or HPLC mobile phase absorbs. The analyte concentration range can be defined as the ratio of the maximum to minimum concentration. Due to the limitations discussed above, the dynamic range of a typical detector is limited to about five orders of magnitude.

A wide dynamic range detector is necessary when very small and very large peaks need to be quantitated in the same chromatogram. For example, the related substances assay commonly performed for the analysis of impurities and degradants in pharmaceutical substances relies on the ability of the absorbance detector to provide sufficient dynamic range to capture both the impurities (concentrations≤0.1%) and the active ingredients (concentrations nominally 100%).

Assays are commonly developed to provide a peak height for the principal component, e.g., an Active Pharmaceutical Ingredient (API), within an acceptable error range with respect to an ideal linear calibration curve. Absorbance detectors are commonly characterized by a linearity specification based on ASTM E685-79 which defines a protocol to determine the absorbance at which the deviation from linearity is five percent.

Absorbance detector design is close to limits imposed by the physics of available components (light sources, photodetectors etc.), the constraints on cell volume required to maintain chromatographic resolution, and market-driven requirements of spectral range and resolution. Currently available absorbance detectors exhibit noise that approaches the shot noise limit of the semiconductors used as photodetectors. Further reduction of the noise will require more intense light sources and/or cooling of the photodiodes to reduce the shot noise limit. As a result, significant improvement of the noise limit through detector design is unlikely and would result in increased cost and/or complexity.

Long path length light-guiding flow cells offer a way to increase concentration sensitivity for a given baseline noise. Unfortunately, the high concentration limit, set by the detector's linear absorbance range, is reduced by the same amount, so that the concentration range remains the same. Moreover, if the mobile phase absorbs, the concentration range will actually be less with a longer cell.

Accordingly, there remains a need for absorbance detectors and associated methods that provide a wide dynamic range.

SUMMARY

The present invention is generally directed to methods for improving the dynamic range of an absorbance detector and absorbance detectors having improved dynamic range. In an exemplary embodiment, the methods include receiving calibration data for a plurality of samples, the calibration data including an absorbance for a concentration of each of the samples, calculating a contribution of stray light to the calibration data, and correcting subsequent data by removing at least a portion of the contribution of stray light. For example, correcting subsequent data by removing the contribution of stray light can provide a gain in the range of about 1.5 AU to about 2.1 AU.

In some embodiments, the step of calculating a contribution of stray light to the calibration data can include regressing the set of calibration data against a relationship between concentration and absorbance. The relationship between concentration and absorbance can include the contribution of stray light to the absorbance of the sample. For example, the relationship between concentration and absorbance can be expressed by the equation set forth below:

$$A = \log_{10}\left[\frac{(1+S)}{10^{-\varepsilon bC} + S}\right] \qquad \text{Eq. 1}$$

in which A represents an absorbance of a sample, S represents a contribution of stray light to the absorbance of the sample, C represents a molar concentration of the sample, b represents a path length of a detector, and ε represents a molar absorbtivity of the sample.

In some embodiments, the step of correcting subsequent data by removing at least a portion of the contribution of stray light can include receiving subsequent data for a sample, receiving a contribution of stray light to the absorbance of the sample, and transforming an absorbance of the subsequent data based on a relationship between absorbance and stray light. For example, the relationship between absorbance and stray light can be expressed by the equation set forth below:

$$A_{lin} = -\log_{10}\left[\frac{(1 - S(10^A - 1))}{10^A}\right] \qquad \text{Eq. 2}$$

in which A represents the absorbance of a sample, $A_{lin}$ represents a transformed absorbance of a sample, and S represents the contribution of stray light to the absorbance of the sample.

In another aspect, methods for measuring the concentration of a sample are provided. The methods can include receiving absorbance data from a sample, receiving calibration data, the calibration data including a contribution of stray light to the absorbance data, correcting the absorbance data by removing at least a portion of the contribution of stray light to the absorbance data, and calculating a concentration of the sample based on the corrected absorbance data. The relationship between absorbance and stray light can be expressed by Equation 2, above.

In exemplary embodiments, the methods for improving the dynamic range of an absorbance detector and methods for measuring the concentration of a sample include providing an absorbance detector. For example, the absorbance detector can be the detector discussed in more detail below.

In another aspect, an absorbance detector is provided. The absorbance detector can include a flow cell, a light source, and a photodetector. The flow cell can have a chamber configured to receive a sample and to provide a light path through the sample. The light path can have a path length. For example, the path length can be in the range of about 3 mm to about 60 mm, in the range of about 3 mm to about 50 mm, in the range of about 3 mm to about 25 mm, in the range of about 5 mm to about 25 mm, or in the range of about 10 mm to about 25 mm. In exemplary embodiments, the path length can be selected from one of about 5 mm, about 10 mm, about 25 mm, about 50 mm, and about 60 mm. The light source can be configured to direct light into the flow cell and into the light path through the sample. The photodetector can be configured to receive light from the light path through the sample and output a signal based on the received light. The photodetector signal can include a measure of an absorbance of the sample.

The absorbance detector can also be configured to remove at least a portion of a contribution of stray light from the photodetector signal and output a corrected signal. In some embodiments, the absorbance detector can include a processor in communication with a memory. The processor can be configured to receive the contribution of stray light to an absorbance of the sample, store the contribution of stray light in the memory, receive the photodetector signal, transform the photodetector signal to remove at least a portion of the contribution of stray light therefrom, and output the corrected signal. For example, the photodetector signal processor can be configured to transform the photodetector signal based on the relationship between absorbance and stray light expressed in Equation 2, above. The corrected signal can provide a gain in the range of about 1.5 AU to about 2.1 AU.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
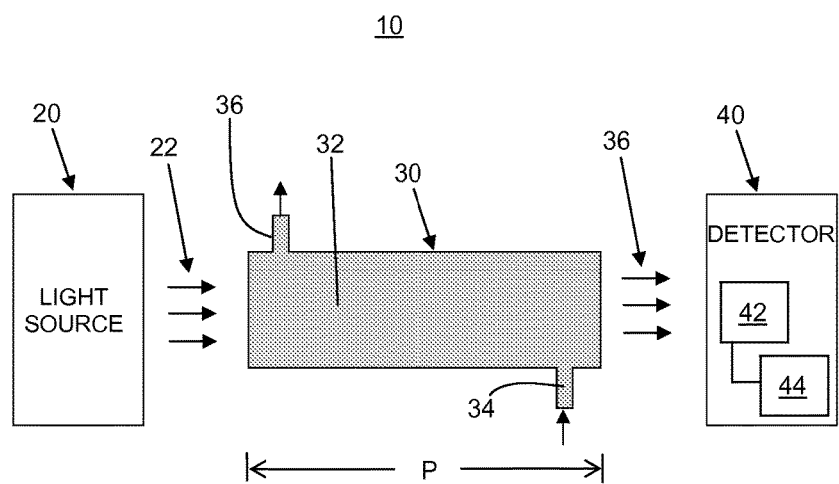
FIG. 1 is a conceptual overview of a measurement system according to an embodiment of the present invention.

The present invention generally provides a method for improving the dynamic range of an absorbance detector and absorbance detectors configured to provide improved dynamic range. A conceptual overview of a measurement system 10 according to an embodiment of the present invention is shown in FIG. 1. A light source 20 provides light beams 22 which pass into and through a flow cell 30. The light source 20 can be any light source capable of providing light of an appropriate spectrum and bandwidth, e.g., a deuterium, tungsten or xenon lamp. The light source 20 can also include various focusing lenses and reflectors.

As the light beams 22 enter the flow cell 30, they pass through a sample in the sample chamber 32. The sample flows into the flow cell 30 through the inlet 34 and flows out of the flow cell 30 through the outlet 36. The light beams traverse a path length P through the flow cell 30. After passing through the flow cell 30, the light beams 36 are received and measured by a detector 40. The detector can be any appropriate detector type, e.g., a silicon photodiode or a photodiode array. In the case of a photodiode array detector, the combined light 36 is wavelength dispersed before it reaches the photodiode array. An exemplary detector is the ACQUITY UPLC® Photodiode Array (PDA) Detector produced by Waters Corporation of Milford, Mass. The light beams 36 that have passed through flow cell 30 are received by the detector 40, which produces an output signal indicative of the light as affected by the sample in the chamber 32. In some embodiments, the detector 40 can include a processor 40 in communication with a memory 44. In other embodiments, the detector 40 can output a signal to a separate processor and memory.

The absorbance of a sample, e.g., a sample flowing through an exemplary flow cell as discussed above, can be defined by $$A = \log_{10}\left[\frac{I_o}{I}\right] = \varepsilon b C \qquad \text{Eq. 3}$$

in which A is the absorbance, $I_o$ is the incident light intensity, I is the transmitted light intensity, C is the molar concentration of the sample, b is the path length of the detector, and $\varepsilon$ is the molar absorbtivity of the sample. The primary signal measured by an absorbance detector is the ratio of the transmitted and incident light intensity, which can be referred to as the transmittance of the flow cell contents.

Figure 2:
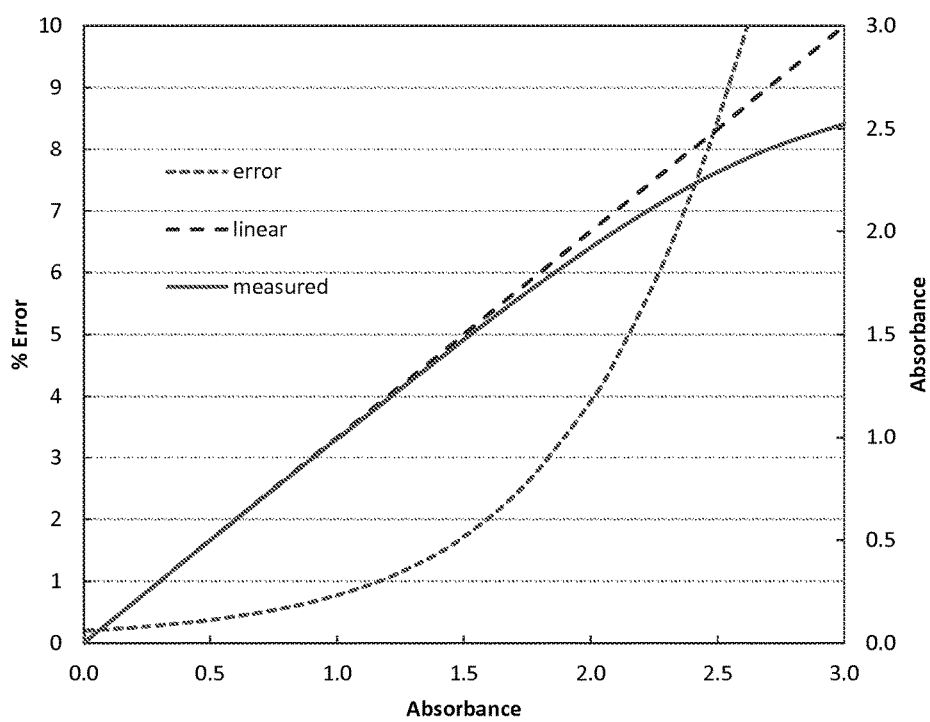
FIG. 2 is an exemplary plot of concentration, absorbance, and percent error for conventional absorbance detectors.

Absorbance detectors are commonly characterized by a linearity specification based on ASTM E685-79 which defines a protocol to determine the absorbance at which the deviation from linearity is five percent. Currently available absorbance detectors, both tunable wavelength and photodiode array, are typically characterized by a linearity specification of less than or equal to about 2.5 AU for the five percent deviation defined by ASTM E685-79. FIG. 2 shows an exemplary calibration curve for a currently available absorbance detector, which also includes a plot of the percent error of the detector. For example, the calibration curve of FIG. 2 represents a detector that reaches an ASTM limit of five percent at an absorbance of about 2.2 AU.

Absorbance detectors for chromatographic applications are typically designed to maximize the efficiency of the optics in order to reduce noise. As a consequence, these absorbance detectors will display finite, but small, stray light. There can also be other instrumental sources of non-linearity in absorbance detectors, e.g., polychromatic light sources, electronic offsets, and mobile phase absorbance. Equation 3 does not include the contribution of stray light or other sources of non-linearity. However, if the source of stray light is modeled as being the detector light source and other sources of non-linearity are modeled as apparent stray light, then Equation 3 can be modified to include the contribution of stray light and apparent stray light on the measured absorbance as set forth below.

$$A' = \log_{10}\left[\frac{(I_o + I_o S)}{(I_o \times 10^{-\varepsilon b C} + I_o S)}\right] \qquad \text{Eq. 4}$$

in which A' represents the measured absorbance of a sample, $I_o$ is the incident light intensity, I is the transmitted light intensity, S represents a contribution of stray light expressed as a fraction of $I_o$, and apparent stray light to the absorbance of the sample, C represents a molar concentration of the sample, b represents a path length of a detector, and $\varepsilon$ represents a molar absorbtivity of the sample. Equation 4 is equivalent to Equation 1, reproduced below.

$$A' = \log_{10}\left[\frac{(1 + S)}{10^{-\varepsilon b C} + S}\right] \qquad \text{Eq. 1}$$

in which A' represents a measured absorbance of a sample, S represents a contribution of stray light to the absorbance of the sample, C represents a molar concentration of the sample, b represents a path length of a detector, and $\varepsilon$ represents a molar absorbtivity of the sample.

As the stray light term in Equation 1 approaches zero, the measured absorbance, A', will approach the ideal absorbance, A, of Equation 3. As the absorbance approaches infinity, i.e., as the sample becomes opaque, the measured absorbance will asymptote to a stray light limit and the measured absorbance can be expressed by the equation set forth below:

$$A' = \log_{10}\left[\frac{1 + S}{S}\right] \qquad \text{Eq. 5}$$

in which A' represents the measured absorbance of a sample and S represents a contribution of stray light and apparent stray light to the absorbance of the sample.

Equation 1 can be rearranged to provide a value of absorbance, $A_{lin}$, that would be measured in the absence of stray light. This relationship between absorbance and stray light can be expressed by Equation 2, reproduced below:

$$A_{lin} = -\log_{10}\left[\frac{(1 - S(10^{A'} - 1))}{10^{A'}}\right] \qquad \text{Eq. 2}$$

in which A' represents the measured absorbance of a sample, $A_{lin}$ represents a transformed absorbance of a sample, and S represents the contribution of stray light to the absorbance of the sample.

Figure 3:
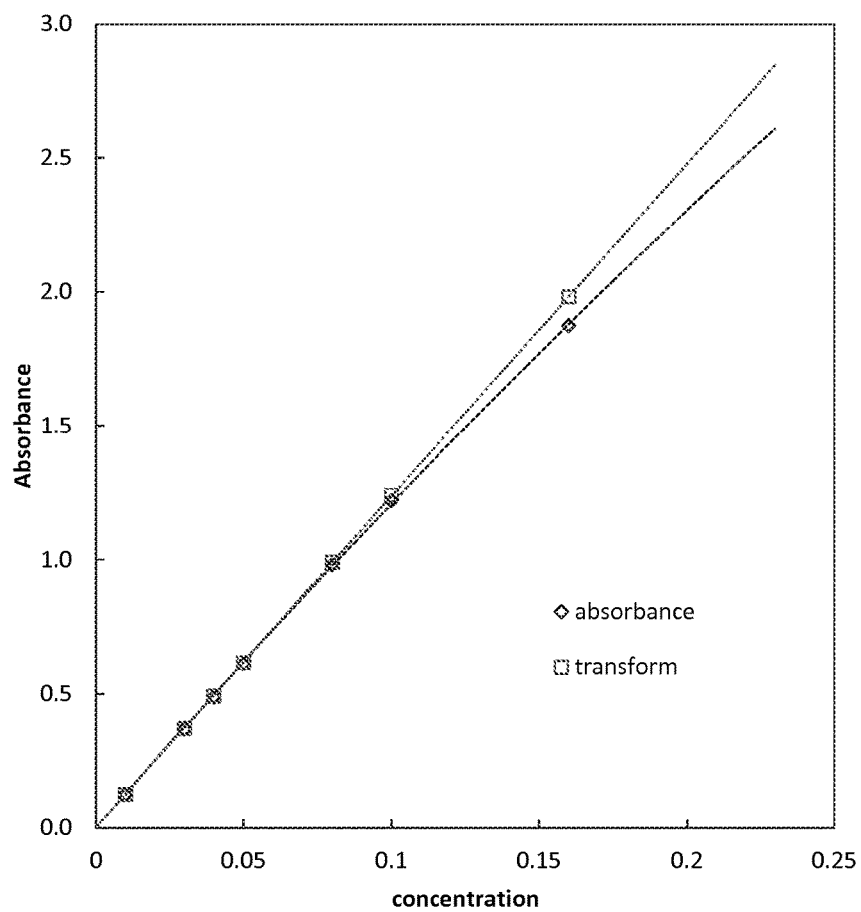
FIG. 3 is an exemplary plot of concentration and absorbance for measured absorbance and transformed absorbance according to an embodiment of the invention.

If the contribution of stray light to the measured absorbance is known, then the measured absorbance can be used to compute an absorbance value which would be obtained in the absence of stray light. The contribution of stray light to the measured absorbance can be determined by regressing absorbance data from an absorbance detector against Equation 1 to provide an estimate of the apparent stray light, S. For example, nonlinear regression can be conducted using commercially available curve fitting programs. An exemplary tool for performing nonlinear regression can be found in the Empower™ 3 Software from Waters Corporation of Milford, Mass., which provides several versions of non-linear calibration curves based on regression analysis. The estimate of the apparent stray light, S, can then be used in Equation 2 to calculate a linearized absorbance, $A_{lin}$, from subsequent absorbance data. FIG. 3 shows an example of absorbance data and data that has been transformed into linearized absorbance data.

Figure 4:
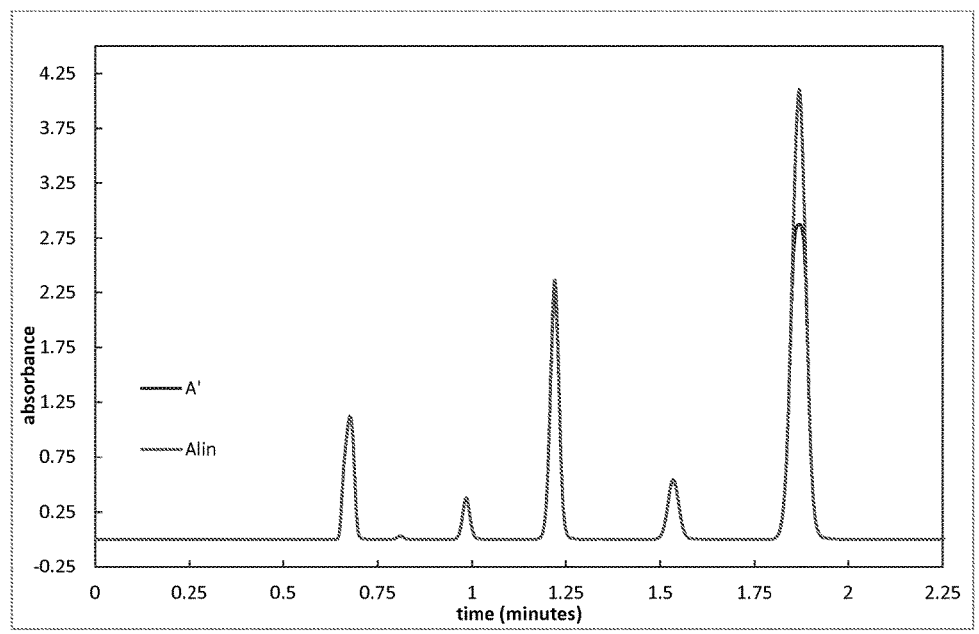
FIG. 4 is an exemplary chromatogram illustrating the effect of an absorbance transformation according to an embodiment of the invention.

FIGS. 2 and 3 illustrate that correction for stray light has a negligible effect at low values of absorbance, e.g., less than about 1 AU. At higher values of absorbance, e.g., greater than about 1.5 AU, the correction for stray light has a significant effect. Exemplary results of a stray light correction according to an embodiment of the present invention are shown in FIG. 4, which shows a chromatogram with large peaks of greater than about 2 AU. Plots of both the measured absorbance data and corresponding corrected data are shown. The widths of the peaks eluting at 1.87 minutes, measured at 4.4% of peak height, are 5.2 and 5.6 seconds for the transformed and measured absorbance chromatograms. The transformation reveals that the degree of peak broadening associated with detector non-linearity is nearly eight percent in this case. In addition to the quantitative error associated with non linearity, the peak broadening decreases chromatographic resolution.

Figure 5:
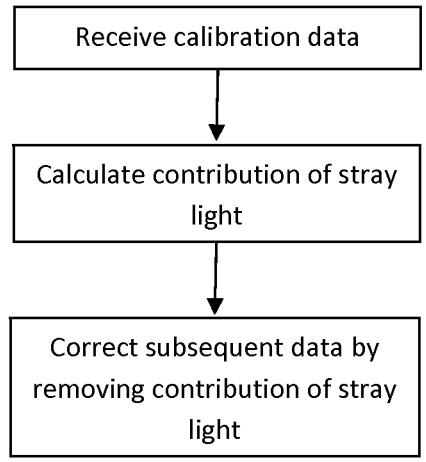
FIG. 5 is a flowchart of a method according to an embodiment of the invention.

In an exemplary embodiment, a method of improving the dynamic range of an absorbance detector can include receiving calibration data for a plurality of samples, calculating a contribution of stray light to the calibration data, and correcting subsequent data by removing at least a portion of the contribution of stray light, e.g., as shown in the flowchart of FIG. 5. The calibration data can include an absorbance value for each of a plurality of sample concentrations. The calibration data can be obtained by running a plurality of samples of known concentrations through the measurement system, e.g., measurement system 10. The calibration data can include, for example, an absorbance for each sample of known concentration. The number of samples can be selected to provide sufficient data to allow for statistical rigor in curve fitting. For example, at least three samples of known different concentrations can be used. For another example, five or more samples of known different concentrations can be used.

The step of calculating a contribution of stray light to the calibration data can include regressing the set of calibration data against a relationship between concentration and absorbance. For example, the relationship between concentration and absorbance can include a contribution of stray light to the absorbance measured by the detector. In an exemplary embodiment, the relationship between concentration and absorbance can be expressed by Equation 1, above.

As discussed above, the relationship between concentration and absorbance can be used to calculate an estimate of the apparent stray light, S. The estimate of apparent stray light can be characteristic of the particular detector, wavelength, and mobile phase combination. Once that estimate is known, then subsequent absorbance data received by the detector can be transformed using Equation 2 to calculate a linearized absorbance, as discussed above.

Figure 6:
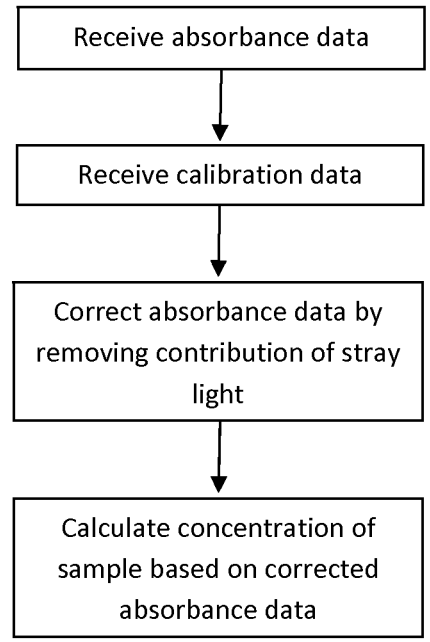
FIG. 6 is a flowchart of a method according to another embodiment of the invention.

In accordance with the methods of improving the dynamic range of an absorbance detector discussed above, exemplary embodiments can include methods for measuring the concentration of a sample. The methods can include receiving absorbance data from a sample, receiving calibration data, the calibration data including a contribution of stray light to the absorbance data, correcting the absorbance data by removing at least a portion of the contribution of stray light to the absorbance data, and calculating a concentration of the sample based on the corrected absorbance data, e.g., as shown in the flowchart of FIG. 6. The relationship between absorbance and stray light can be expressed by Equation 2, above.

In some embodiments, absorbance detectors used in the methods discussed above can be configured to process the photodetector signal to remove the contribution of stray light therefrom and output a corrected signal. For example, the absorbance detector can include a processor in communication with a memory. In other embodiments, the output from the photodetector can be communicated to a separate processor and memory.

For example, the processor can be configured to receive a contribution of stray light to an absorbance of the sample, store the contribution of stray light in the memory, receive the photodetector signal, transform the photodetector signal to remove at least a portion of the contribution of stray light therefrom, and output the corrected signal.

The methods disclosed herein can also be extended to other detectors and detection techniques for which a formal expression can be used to model the non-linearity in the detector signal. In such cases, regression techniques can be used to model the parameters of the non-linearity and a linearized response can be constructed once the model parameters have been estimated. For example, the methods disclosed herein can be extended to fluorescence detectors, electrochemical detectors, or conductivity detectors. In a fluorescence detector, the fluorescence of a sample can be expressed as $$F = F_c(1 - e^{\varepsilon bC}) \qquad \text{Eq. 6}$$

in which F is the fluorescence, $F_c$ is a constant, $\varepsilon$ represents a molar absorbtivity of the sample, b is the path length of the detector, and C is the molar concentration of the sample. $F_c$ represents an instrument specific constant that can account for the light source intensity, the optical efficiency of the detector, and quantum efficiency of the sample.

The $\varepsilon bC$ term in Equation 6 is equivalent to the absorbance of the sample, as noted above with respect to Equation 3. For low values of the absorbance term, i.e., when $\varepsilon bC$ is less than about 0.05, the fluorescence can be approximated as $$F = F_c(\varepsilon bC) \text{ or } F = A \times B \times C \qquad \text{Eq. 7}$$

in which F is the fluorescence, $F_c$ is a constant, $\varepsilon$ represents a molar absorbtivity of the sample, b is the path length of the detector, C is the concentration of the sample, and where A and B are simple proportionality constants. Common practice in fluorescence detection is to operate with samples of low concentration and assume that the response is linear as described by Equation 7. The simplified expression of Equation 7 is commonly used for calibration and quantitation in fluorescence detection. The simplified expression is necessarily limited to solutions with low concentrations.

However, this approximation does not account for the inherent non-linearity of the fluorescence data. Using similar techniques to those discussed above for transformation of absorbance, a linearized fluorescence can be calculated. For example, fluorescence can expressed as $$F = F_c(1 - e^{-B(C)}) \qquad \text{Eq. 8}$$

in which F is the fluorescence, $F_c$ is a constant, B is a constant, and C is the concentration of the sample.

The apparent concentration can be calculated according to the following equation $$C = \frac{-\ln\left(1 - \frac{F}{A}\right)}{B} \quad \text{Eq. 9}$$

in which C is the apparent concentration, F is the detected fluorescence, and where A and B are constants. Equation 9 can be substituted into Equation 7 to provide the following expression $$F_{lin} = A \times B\left(\frac{-\ln\left(1 - \frac{F}{A}\right)}{B}\right) \quad \text{Eq. 10}$$

$F_{lin}$ is the linearized fluorescence, F is the detected fluorescence, and A and B are the constants determined from a regression analysis.

The methods disclosed herein can be implemented, in an exemplary embodiment, using the Empower™ 3 Software from Waters Corporation of Milford, Mass. Elements of such an implementation can include collection of the calibration data, storage of that data in a secure database to ensure the traceability of both the calibration and quantitation data, creation of a transformed, e.g., linearized, data channel within either the detector or within the Empower™ software as a derived channel by applying the stray light correction or other correction, and retaining the transformed and original data channels. The calibration, collection, and linearization of the data can be controlled and secured within detectors and software products available from Waters Corporation.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for measuring the concentration of a sample comprising:
  receiving absorbance data measured for a sample;
  receiving calibration data, the calibration data comprising a contribution of stray light to the absorbance data;
  correcting the absorbance data by removing at least a portion of the contribution of stray light from the absorbance data; and
  calculating a concentration of the sample based on the corrected absorbance data,
  wherein correcting the absorbance data by removing the contribution of stray light to the absorbance data comprises:
    transforming the absorbance data based on a relationship between absorbance and stray light, wherein that relationship is expressed by the equation set forth below:

$$A_{lin} = -\log_{10}\left[\frac{(1 - S(10^A - 1))}{10^A}\right],$$

in which:
  A represents the absorbance of a sample,
  $A_{lin}$ represents a transformed absorbance of the sample, and
  S represents the contribution of stray light to the absorbance of the sample.

2. The method of claim 1, further comprising:
  providing an absorbance detector, the absorbance detector comprising
  a flow cell having a chamber configured to receive the sample, the flow cell being configured to provide a light path through the sample, the light path having a path length,
  a light source configured to direct light into the flow cell and into the light path through the sample, and
  a photodetector configured to receive light from the light path through the sample and output a signal based on the received light.

3. The method of claim 2, wherein the absorbance detector is configured to (i) remove a contribution of stray light from the photodetector signal and (ii) output a corrected signal.

4. The method of claim 3, wherein the absorbance detector further comprises a processor in communication with a memory, the processor configured to (i) receive the contribution of stray light to an absorbance of the sample, (ii) store the contribution of stray light in the memory, (iii) receive the photodetector signal, (iv) transform the photodetector signal to remove the contribution of stray light therefrom, and (v) output the corrected signal.

5. The method of claim 1, wherein correcting subsequent data by removing the contribution of stray light provides generates a corrected signal operative to provide a gain of about 1.5 AU to about 2.1 AU.

6. A method for improving dynamic range of an absorbance detector comprising:
  receiving calibration data for a plurality of samples, the calibration data comprising an absorbance measured for a concentration of each of the samples;
  calculating a contribution of stray light to the calibration data;
  correcting subsequent data by removing at least a portion of the contribution of stray light,
  wherein calculating a contribution of stray light to the calibration data comprises:
    regressing the set of calibration data against a relationship between concentration and absorbance, wherein the relationship includes the contribution of stray light to the absorbance of the samples,
    wherein the relationship between concentration and absorbance is expressed by the equation set forth below:

$$A = \log_{10}\left[\frac{(1 + S)}{10^{-\varepsilon bC} + S}\right],$$

in which:
  A represents an absorbance of a sample,
  S represents a contribution of stray light to the absorbance of the sample,
  C represents a molar concentration of the sample,
  b represents a path length of a detector, and
  E represents a molar absorbtivity of the sample.

7. The method of claim 6, wherein correcting subsequent data by removing the contribution of stray light comprises:

receiving subsequent data for a sample;
receiving a contribution of stray light to the absorbance of the sample;
transforming an absorbance of the subsequent data based on a relationship between absorbance and stray light.

8. The method of claim 7, wherein the relationship between absorbance and stray light is expressed by the equation set forth below:

$$A_{lin} = -\log_{10}\left[\frac{(1 - S(10^A - 1)}{10^A}\right]$$

in which:
A represents the absorbance of a sample,
$A_{lin}$ represents a transformed absorbance of the sample, and
S represents the contribution of stray light to the absorbance of the sample.

9. The method of claim 6, further comprising:
providing an absorbance detector, the absorbance detector comprising
a flow cell having a chamber configured to receive a sample, the flow cell being configured to provide a light path through the sample, the light path having a path length,
a light source configured to direct light into the flow cell and into the light path through the sample
a photodetector configured to receive light from the light path through the sample.

10. An absorbance detector comprising:
a flow cell having a chamber configured to receive a sample, the flow cell being configured to provide a light path through the sample, the light path having a path length,
a light source configured to direct light into the flow cell and into the light path through the sample, and
a photodetector configured to receive light from the light path through the sample and output a signal based on the received light;
wherein the absorbance detector is configured to (i) remove a contribution of stray light from the photodetector signal and (ii) output a corrected signal,
wherein the photodetector signal processor is configured to transform the photodetector signal based on a relationship between absorbance and stray light expressed by the equation set forth below:

$$A_{lin} = -\log_{10}\left[\frac{(1 - S(10^A - 1)}{10^A}\right],$$

in which:
A represents an absorbance of a sample,
$A_{lin}$ represents a transformed absorbance of the sample, and
S represents the contribution of stray light to the absorbance of the sample.

11. The absorbance detector of claim 10, further comprising:
a processor in communication with a memory, the processor configured to (i) receive a contribution of stray light to an absorbance of the sample, (ii) store the contribution of stray light in the memory, (iii) receive the photodetector signal, (iv) transform the photodetector signal to remove the contribution of stray light therefrom, and (v) output the corrected signal.

12. The absorbance detector of claim 10, wherein the photodetector signal comprises a measure of an absorbance of the sample.

13. The absorbance detector of claim 10, wherein the corrected signal provides a gain in the range of about 1.5 AU to about 2.1 AU.

* * * * *